United States Patent [19]

Collina et al.

[11] 4,067,908

[45] Jan. 10, 1978

[54] PROCESS FOR THE PRODUCTION OF FORMALDEHYDE

[75] Inventors: Amilcare Collina; Emanuele Malfatti; Antonio Cappelli, all of Milan, Italy

[73] Assignee: Montedison S.p.A., Milan, Italy

[21] Appl. No.: 578,873

[22] Filed: May 19, 1975

Related U.S. Application Data

[63] Continuation of Ser. No. 359,356, May 11, 1973, abandoned.

[30] Foreign Application Priority Data

May 15, 1972 Italy .......................................... 24339

[51] Int. Cl.² ............................................. C07C 45/16
[52] U.S. Cl. ................................................. 260/603 C
[58] Field of Search ......................... 260/603 R, 603 C

[56] References Cited

U.S. PATENT DOCUMENTS

| 1,744,295 | 1/1950 | Ahlbeck ......................... 260/603 HF |
| 2,519,788 | 8/1950 | Payne ............................. 260/603 HF |
| 2,812,308 | 11/1957 | Shelton et al. ................. 260/603 HF |

Primary Examiner—Bernard Helfin
Assistant Examiner—W. B. Lone
Attorney, Agent, or Firm—Stevens, Davis, Miller & Mosher

[57] ABSTRACT

A process is provided for the production of formaldehyde by oxidizing methanol in the presence of a catalyst containing metal oxides wherein the feed stream is admixed, outside the reaction stage, with at least one portion of the reaction product.

5 Claims, 1 Drawing Figure

U.S. Patent
Jan. 10, 1978
4,067,908
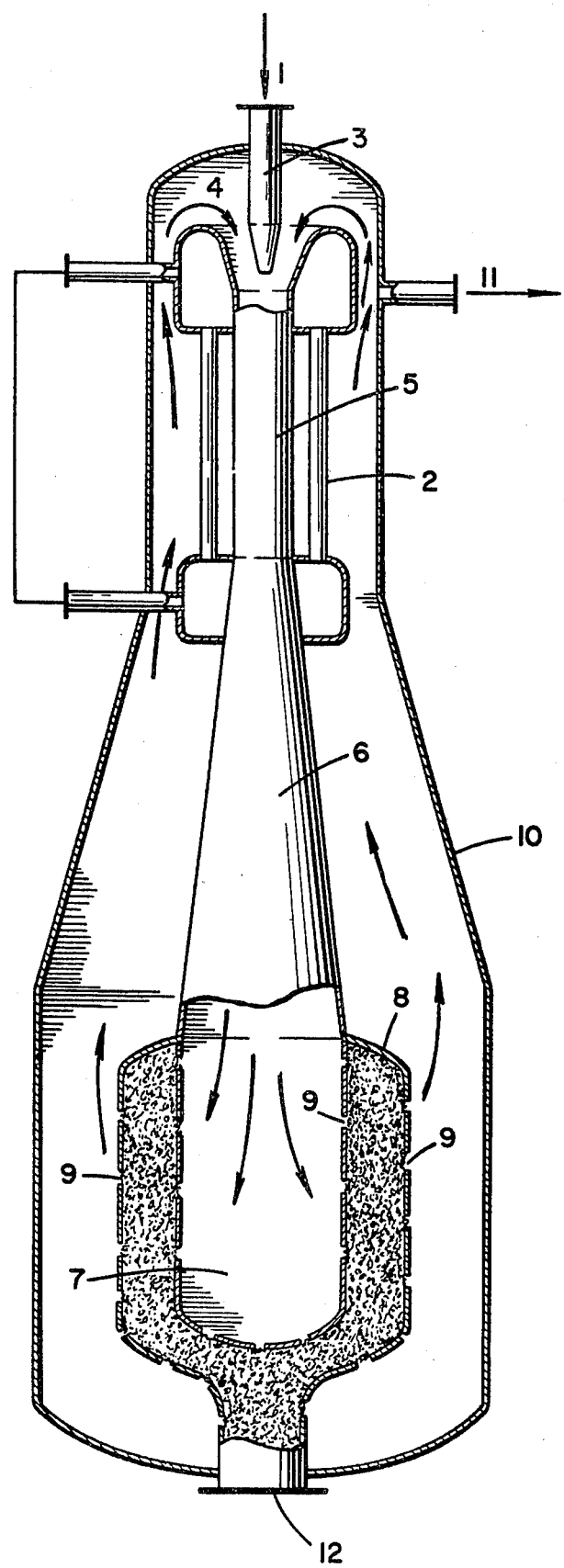

PROCESS FOR THE PRODUCTION OF FORMALDEHYDE

This is a continuation of application Ser. No. 359,356, filed 5/11/73, now abandoned.

This invention relates to an improved process for the production of formaldehyde by oxidation of methanol with air or other oxygen-containing gas, at temperatures within the range of 200° C to 400° C, in the presence of a catalyst containing metal oxides. More particularly, the invention relates to an apparatus adapted for use in practicing the improved process.

It is known to oxidize methanol in a reactor provided with a bundle of tube filled with a catalyst, containing a mixture of oxides, of different metals, for instance Pe, Mo, Co.

It is also known from U.S. Pat. No. 2,504,402 to let the reacting mixture of oxidizing gas and methanol pass through several catalyst layers in series, regulating the course of the reaction by means of cooling coils and injections of fresh methanol (or its mixtures with the oxidizing gas) into the interspaces between the layers.

In these processes the concentration of the formaldehyde in the gases flowing out of the reactor, must attain a minimum level of from 5% to 6% by volume. Otherwise the absorption apparatus down stream of the reactor must have such large dimensions that is very expensive.

In order to obtain a concentration of 5% to 6% formaldehyde in the effluent gases, concentrations of the same order of magnitude (6–6.5% by volume) of methanol are required in the gaseous mixture fed to the reaction zone. Such concentrations of methanol are very near the explosive range. Moreover, with such concentrations of methanol it is necessary to carefully control the temperature of the reaction to avoid excessive temperatures and too rapid reaction rates and to limit the thickness of the catalyst layers and to increase the number of layers thereof. When reactors with a plurality of catalyst layers in series are used, it is necessary to provide each layer of the catalyst with the corresponding temperature control devices (by means of external cooling and injection of quench gases) with the result that a series of complicated and costly apparatuses are required.

A further disadvantage of the prior art apparatus is that further pressure drops are required to effectively distribute the gas over the catalyst.

Still another drawback of the apparatuses of the prior art is that construction problems are encountered in installing the large diameter pipes required by the apparatus. Such pipes are subject to high thermal expansion.

As the oxidation of methanol is performed, in general, at a low pressure, a further disadvantage is that a wide area is required for the apparatuses and the corresponding piping.

Therefore, an object of this invention is to provide a process for making formaldehyde by the oxidation of methanol which is devoid of the foregoing disadvantages and produces a high yield of product in a single apparatus.

Other objects will become apparent from the following descriptions with reference to the accompany drawing illustrating one embodiment of the apparatus provided by the invention.

It has now been found that the above objects may be achieved by providing an improved process for the production of formaldehyde through the oxidation of methanol with air or other oxygen-containing gas, at temperatures within the range of about 200° C to 400° C in the presence of a catalyst containing metal oxides, wherein the feed stream is admixed, outside the reaction stage, with at least one portion of the reaction product coming directly from the reaction stage, and that at least one portion of the resulting mixture is directly conveyed towards the reaction stage. In this way, a recycle of at least one portion of the raw reaction product from the outlet of the reaction stage to the inlet of the reaction stage is achieved. The cycle may be controlled in a simple and practical way through a heat exchange and it may be performed by using a compressor, an injector or any other suitable device external of the reaction stage.

By means of this recycle, it is possible to have a relatively low concentration of methanol inside the reactor itself and still produce suitable concentrations of formaldehyde leaving the reactor.

This avoids the development of excessively high temperatures on the catalyst bed and excessively high reaction rates. Consequently, devices for the control of the temperature may be reduced or eliminated. For example, cooling coils are not required if the process is an adiabatic one.

The improved process provided by the invention is more flexible, i.e. the output level can vary within a wide range, and makes it possible to make installations of high output level by using a reactor in which the number of catalyst layers can be reduced conveniently to just a single one. In this way it is possible to avoid the use of costly diathermic oils in the reaction stage to avoid stopping of the reaction.

The regulation of the temperature may be conveniently realized by cooling at least one portion of the raw product to be recycled, so that the initial contact temperature with the catalyst is between about 220° C and 300° C.

The recycle and feed streams are mixed together in such proportions as to achieve in the mixture coming into contact with the catalyst, a molar ratio of formaldehyde to methanol of between 0.3 and 5.

The space velocity of the gases impinging the catalyst is suitably between 8,000 and 20,000 $h^{-1}$ and preferably between 10,000 and 15,000 $h^{-1}$, wherein space velocity is defined as:

$$\frac{\text{Normal m}^3 \text{ of gas impinging the catalyst per hour}}{\text{m}^3 \text{ of apparent volume of the catalyst}}$$

The catalyst may be arranged in various ways inside the reactor without thereby falling outside the scope of the invention. According to a preferred embodiment of the invention, the reaction is performed in a centrifugal radial flow reactor.

According to a most preferred embodiment, the reaction is performed in an apparatus which, within one single shell has the following parts:

a centrifugal radial flow catalyst basket with a substantially cylindrical inside cavity, one end of the cavity being located immediately downstream of the terminal end of the diffuser;

an outside jacket substantially co-axial with the injector and with the basket, which jacket conveyes at least part of the gases, coming from the basket, towards the inlet of the injector;

a heat exchanger in which at least a portion of the recycling gases, coming from the basket, directly exchanges heat with another fluid.

As fluid for the heat exchanger may be used a fluid alien to the reaction, for instance water, or a fluid involved in the reaction, for example, the feed gases containing the reactants.

The just described apparatus makes it possible to obtain a low power consumption, a good distribution of the gas on the catalyst, lower pressure drops, a simplification of the problems connected with thermal expansions, a reduction of the areas and volumes engaged, as well as a simplification in the choice of the materials. In fact there may be used in a satisfactory way normal carbon steel in substitution for the costly alloy steels used in most prior art apparatuses. An example of an apparatus provided by the invention is illustrated in FIG. 1. Of course, this example is not to be taken as limiting in any way the scope of this invention.

As will be noted in said FIG. 1, the axes of the injector, the basket, the heat exchanger and the jacket coincide substantially with one single vertical rectilinear axis.

The following example is given merely for illustrative purposes and does not limit in any way the scope of the invention.

EXAMPLE 1

Referring now to FIG. 1, the feed mixture, coming from source 1 and containing 6.79% by weight $CH_3OH$, 10.15% by weight $O_2$ and 78.84% by weight $N_2$ enters nozzle 3 of the reactor and draws the recycle stream 4 (compressing it) along with it. The mixture enters mixing chamber 5 and then passes into diffuser 6.

From there the flow reaches chamber 7 which consists of the internal cavity of the catalytic centrifugal radial flow basket 8. This chamber is so dimensioned as to act, for all practical purposes, as a gas distributor, and having pressure drops quite negligible in comparison with the ones of the catalytic bed.

Through orifice 9, the gases reach the catalyst, which contains oxides of iron and molybdenum and react in an adiabatic way. They then pass through jacket 10 which conveyes the reacted gases directly to the heat exchanger 2 where a stream of cooling water is converted into steam.

The reacted gas divides itself at this point into two streams: the one (11) definitively discharges from the reactor and passes to the subsequent process operations (scrubbing, separation of the products, etc.); the other (4) forms, as previously indicated, the recycle. The opening 12 serves for the fast unloading of the exhausted catalyst.

Formaldehyde percentage in the gases leaving the reactor is 6.03% by weight.

Although the invention has been described with reference to particular forms of embodiment, it is understood that modifications may be introduced without thereby falling outside the spirit of the inventive idea of this invention.

What is claimed is:

1. In a process for oxidizing methanol to formaldehyde wherein a gaseous feed stream containing a mixture of methanol and air is heated to from 200° C. to 400° C. and passed over a metal oxide catalyst bed which promotes substantially complete oxidation of the methanol to formaldehyde and the resulting formaldehyde is separated from the gaseous oxidation product, the improvement which comprises recycling only a cooled portion of said oxidation product to the feed stream before any formaldehyde has been separated therefrom in an amount which provides a molar ratio of formaldehyde to methanol of between 0.3 and .5 in the mixture of the recycled portion of the oxidation product with the feed stream and passing this mixture over the said catalyst bed.

2. The process of claim 1 wherein the temperature of said mixture of the feed stream and recycled oxidation product is between 220° and 300° C.

3. The process of claim 1 wherein the space velocity of said mixture is from 8,000 to 20,000 $h^{-1}$.

4. The process of claim 1 wherein the catalyst is arranged in a radial flow basket.

5. The process of claim 1 wherein the space velocity of the mixture passing over the catalyst bed is from 10,000 to 15,000 $h^{-1}$.

* * * * *